United States Patent [19]

Jessel, Jr. et al.

[11] Plant 4,227

[45] Mar. 21, 1978

[54] CHRYSANTHEMUM PLANT

[75] Inventors: Walter H. Jessel, Jr., Grantsville, W. Va.; William E. Duffett, Salinas, Calif.

[73] Assignee: Yoder Brothers, Inc., Barberton, Ohio

[21] Appl. No.: 762,730

[22] Filed: Jan. 26, 1977

[51] Int. Cl.[2] ..... A01H 5/00

[52] U.S. Cl. ..... Plt./75

[58] Field of Search ..... Plt./69, 75

*Primary Examiner*—Robert E. Bagwill

*Attorney, Agent, or Firm*—Donald D. Jeffery

[57] ABSTRACT

A chrysanthemum plant having flat capitulum form and pompon capitulum type, bronze ray floret color; upright branching habit and relatively tall plant height; permanence of inflorescence of 14–21 days, and good tolerance of inflorescence to frost damage.

3 Drawing Figures

1

The present invention comprises a new and distinct cultivar of *Chrysanthemum morifolium,* Ramat., hereinafter referred by the cultivar name Zest (#74054004).

Zest is a product of a planned breeding program which had the objective of creating cultivars with pompon capitulum type, short height, spreading branching pattern, durable inflorescence, short (6 to 7 week) flowering response period, and intense bronze and red-bronze ray floret color with minimal color oxidation under outdoor natural season conditions.

Zest was originated from a cross made in a controlled breeding program in Barberton, Ohio in the year 1973. The male parent was #73337003 (unnamed seedling), a red-bronze pompon originated by the present inventors from a cross between #72074M01 (unnamed seedling) and #72018003 (unnamed seedling). The female parent was #73274001 (unnamed seedling), an orange-bronze pompon originated by the present inventors from a cross between #72037012 (unnamed seedling) and #72054006 (unnamed seedling). #72074M01, #72018003, #72037012 and #72054006 were all products of the breeding program of the present inventors.

Zest was discovered and selected as a flowering plant within the progeny of the stated cross by Walter H. Jessel, Jr. on May 4, 1974 in an outdoor field in Ft. Myers, Fla.

The first act of asexual reproduction of Zest was accomplished when vegetative cuttings were taken from the initial selection in July, 1974 in a controlled environment in Barberton, Ohio by a technician working under formulations established and supervised by William E. Duffett and Walter H. Jessel, Jr. Horticultural examination of selected units initiated Oct. 7, 1974 has demonstrated that the combination of characteristics as herein disclosed for Zest are firmly fixed and are retained through successive generation of asexual reproduction.

Zest has not been observed under all possible environmental conditions. The phenotype may vary significantly with variations in environment such as temperature, light intensity, and daylength. The following observations, measurements, and comparisons describe plants grown in a field in Barberton, Ohio under conditions which are generally described in *Local Climatological Data, Annual Summary With Comparative Data,* Akron, Ohio, U.S. Department of Commerce, National Oceanic and Atmospheric Administration, Environmental Data Service, Washington, D.C. 1974, 1975, 1976, and *Tables of Sunrise, Sunset, and Twilight.* Supplement to the American Emphemeris, 1946., U.S. Naval Observatory, Washington, D.C., pg. 103.

2

The following traits have been repeatedly observed and are determined to be basic characteristics of Zest which in combination distinguish this chrysanthemum as a new and distinct cultivar:

1. Flat capitulum form.
2. Pompon capitulum type.
3. Bronze ray floret color.
4. Diameter across face of capitulum up to 60 mm.
5. Permanence of inflorescence ranging from 14 to 21 days under average natural season outdoor flowering conditions.
6. Tall plant height (requiring 1–2 long day weeks prior to short days and 1 application of 2500 ppm B9-SP to attain a flowered plant height of 30 to 40 cm).
7. Semi-upright branching pattern.
8. Good tolerance of inflorescence to frost damage.
9. Average natural season flowering date of September 28.
10. Average flowering response period of 7 weeks in photoperiodic controlled flowering programs.

The accompanying photographic drawings show typical inflorescence and foliage characteristics of Zest, with the colors being as nearly true as possible with color illustrations of this type. Sheet 1 is a color photograph of Zest. Sheet 2 is a black and white photograph showing three views, enlarged, of the capitulum of Zest. Sheet 3 is a black and white photograph showing the foliage, enlarged, of Zest at three stages of growth.

Of the many commercially available cultivars known to the present inventors, the most similar existing cultivars in comparison to Zest are Minnautumn (#21620E07; unpatented) and Pancho (#21610E04; unpatented). Reference is made to attached Chart A which compares certain characteristics of Zest with the same characteristics of the above identified cultivars. General comparisons are as follows:

1. In comparison to Minnautumn, Zest has different capitulum type, later natural season flower date, taller plant height, smaller diameter across face of capitulumn, and more upright branching habit. The ray floret color and the capitulum form of Zest are similar to those of Minnautumn.

2. In comparison to Pancho, Zest has different ray floret color, capitulum type, and earlier natural season flower date. The capitulum form, plant height, diameter across face of capitulum, and branching pattern of Zest are similar to those of Pancho.

In the following description, color references are made to The Munsell Limit Color Cascade, 1972 edition. The color values were determined between 9:30 and 10:00 A.M. on Oct. 4, 1976 under 120 foot-candle light intensity at Barberton, Ohio.

Botanical classification: *Chrysanthemum morifolium,* Ramat., cv Zest.

Reproductive organs:

*Androecium.*—Present disc florets; scant pollen.

*Gynoecium.*—Present both ray and disc florets.

Plant

General appearance: semi-upright; tall height.

Duration and texture: herbaceous; perennial.

Foliage (See Sheets 1 and 3):

*Color (abaxial).*—Between 23-13 and 22-14.

*Color (adaxial).*—22-12 overcast with white.

CHART A

COMPARISON OF ZEST, MINNAUTUMN AND PANCHO

| CULTIVAR | RAY FLORET COLOR | CAPITULUM FORM AND TYPE | AVERAGE NATURAL SEASON FLOWER DATE | PLANT HEIGHT | DIAMETER ACROSS FACE OF CAPITULUM | BRANCHING PATTERN |
|---|---|---|---|---|---|---|
| ZEST | Red-bronze | Flat Pompon | September 28 | Tall, from 30 to 40 cm. | 45 to 60 mm. | Semi-upright |
| MIN-NAUTUMN | Red-bronze | Flat Decorative | September 25 | Short, from 25 to 30 cm. | 50 to 65 mm. | Semi-spreading |
| PANCHO | Orange-bronze | Flat Decorative | October 1 | Tall, from 30 to 40 cm. | 45 to 60 mm. | Semi-upright |

COMPARISONS MADE OF PLANTS GROWN UNDER NATURAL SEASON OUTDOOR FIELD CONDITIONS IN BARBERTON, OHIO

Inflorescence

Capitulum (See Sheets 1 and 2).

*Form.*—Flat.

*Type.*—Pompon (commercial double).

*Permanence.*—14–21 days.

*Diameter across face.*—45 to 60 mm.

Corolla of ray floret:

*Persistence.*—Resists shatter.

*Color (abaxial).*—Ranging from 36-14 streaked over 31-10 (newly opened florets) oxidizing quickly to 35-14 streaked lightly over 31-10; general tonality ranging from 33-11 to 33-12.

*Color (adaxial).*—31-14 over 28-9.

We claim:

1. A new and distinct cultivar of chrysanthemum known by the cultivar name Zest and characterized particularly as to uniqueness by the combined characteristics of flat capitulum form; pompon capitulum type; bronze ray floret color; diameter across face of capitulum up to 60 mm; permanence of inflorescence ranging from 14 to 21 days; tall plant height; semi-upright branching pattern; good tolerance of inflorescence to frost damage; average natural season flowering date of September 28; and average flowering response period of 7 weeks in photoperiodic controlled flowering programs.

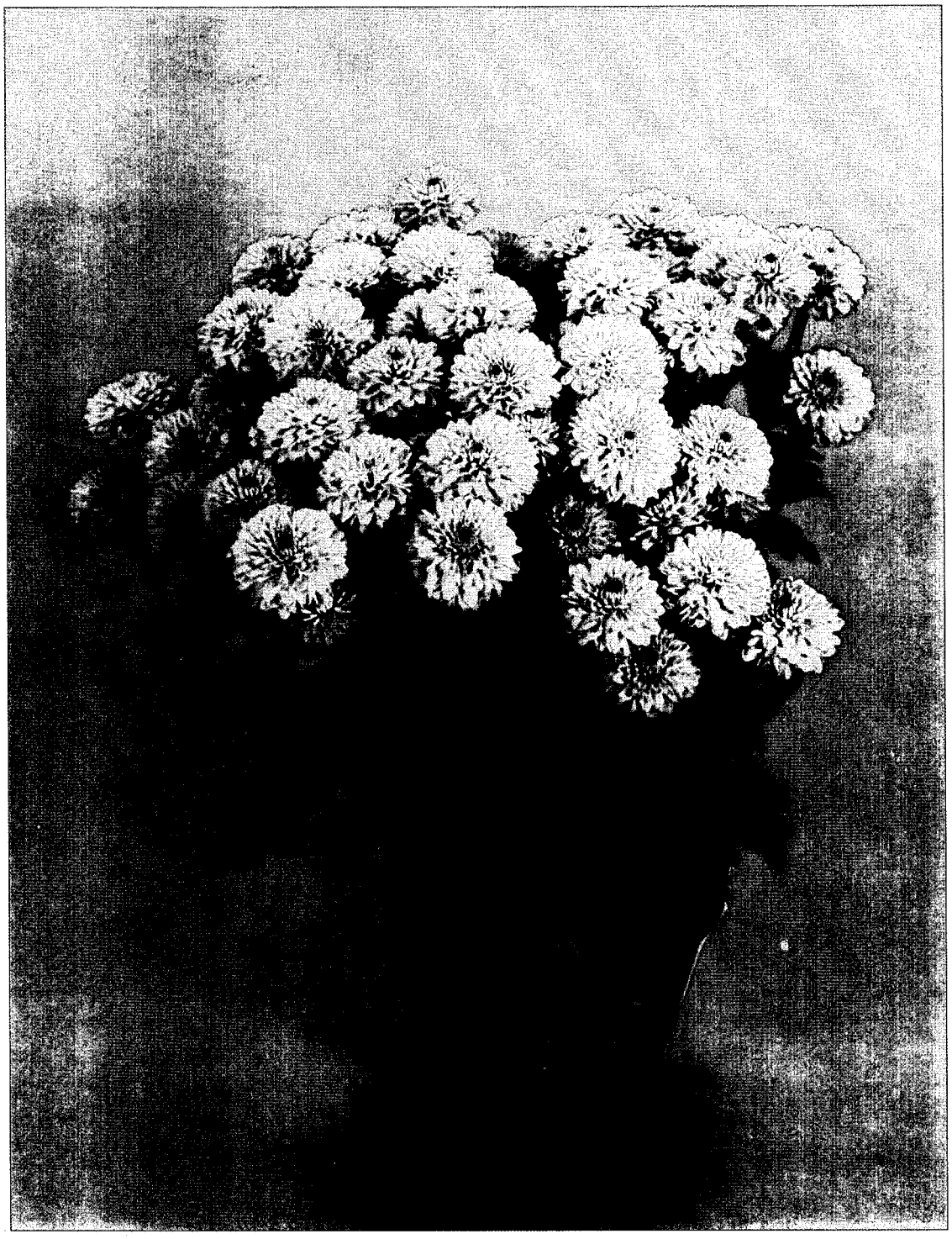

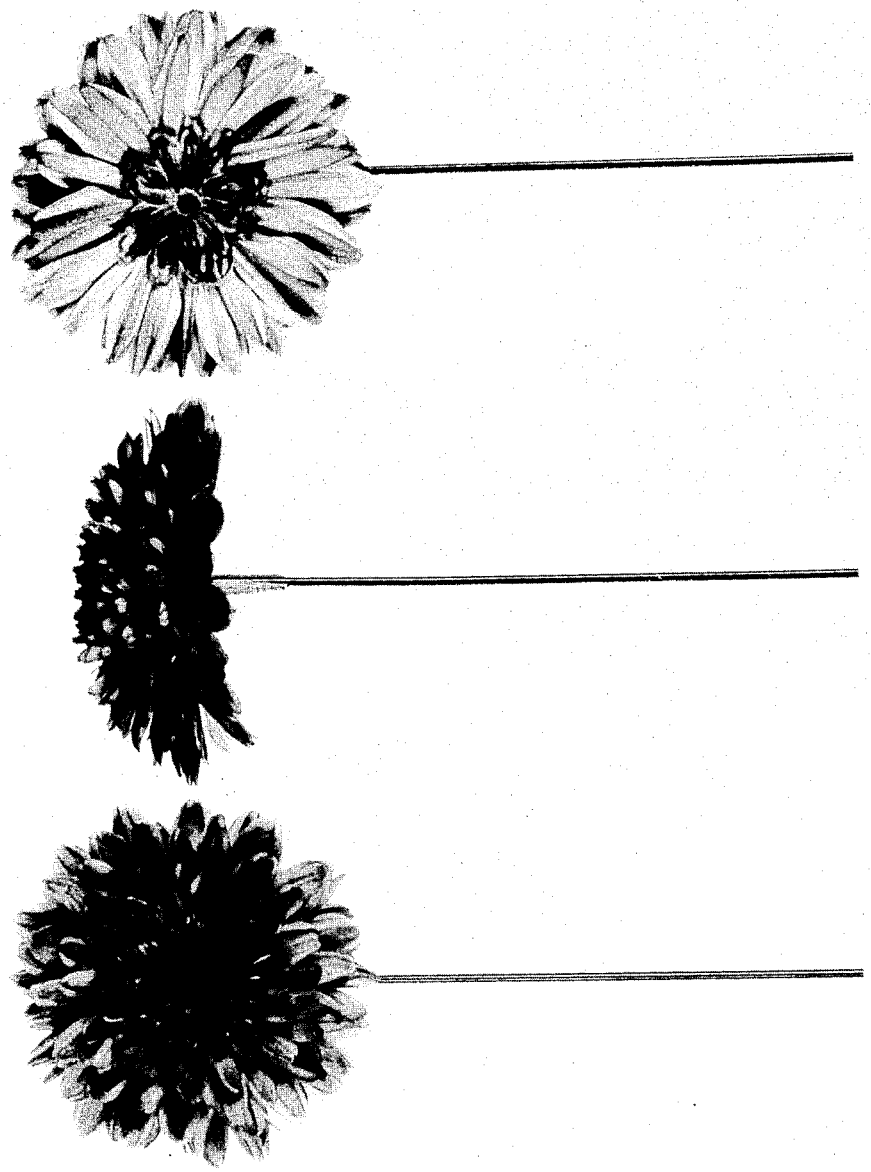

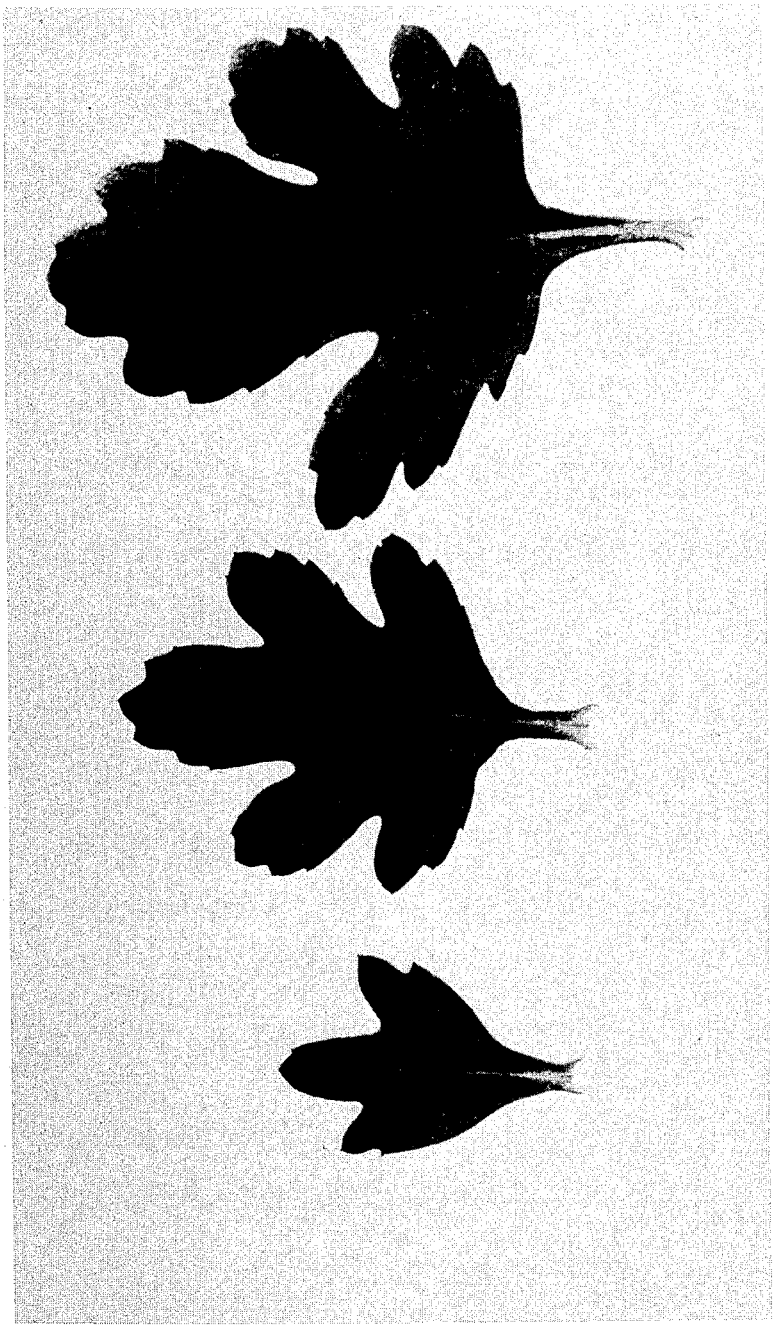

* * * * *